(12) United States Patent
Sakaguchi et al.

(10) Patent No.: US 8,585,583 B2
(45) Date of Patent: Nov. 19, 2013

(54) WORKING MECHANISM FOR MEDICAL MANIPULATOR

(75) Inventors: Akira Sakaguchi, Fujinomiya (JP); Hiroaki Sano, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 1457 days.

(21) Appl. No.: 12/196,755

(22) Filed: Aug. 22, 2008

(65) Prior Publication Data

US 2009/0054726 A1 Feb. 26, 2009

(30) Foreign Application Priority Data

Aug. 23, 2007 (JP) ................................ 2007-216893

(51) Int. Cl.
*A61B 1/00* (2006.01)
*A61B 1/04* (2006.01)

(52) U.S. Cl.
USPC ............................ 600/104; 600/127; 600/106

(58) Field of Classification Search
None
See application file for complete search history.

(56) References Cited

U.S. PATENT DOCUMENTS

| | | | |
|---|---|---|---|
| 5,808,665 A * | 9/1998 | Green ............................ | 348/65 |
| 5,976,122 A * | 11/1999 | Madhani et al. ................ | 606/1 |
| 6,331,181 B1 * | 12/2001 | Tierney et al. ................ | 606/130 |
| 6,994,716 B2 * | 2/2006 | Jinno et al. ..................... | 606/170 |
| 7,314,473 B2 | 1/2008 | Jinno et al. | |
| 8,154,239 B2 * | 4/2012 | Katsuki et al. ................ | 318/565 |
| 2007/0138992 A1 * | 6/2007 | Prisco et al. ............. | 318/568.21 |
| 2007/0156019 A1 * | 7/2007 | Larkin et al. .................. | 600/104 |
| 2009/0163948 A1 * | 6/2009 | Sunaoshi et al. ............. | 606/205 |

FOREIGN PATENT DOCUMENTS

| | | |
|---|---|---|
| JP | 8-291482 | 11/1996 |
| JP | 11-12966 | 1/1999 |
| JP | 2002-317389 | 10/2002 |
| JP | 2003-84212 | 3/2003 |
| JP | 2004-105451 | 4/2004 |
| JP | 2006-192281 | 7/2006 |

OTHER PUBLICATIONS

Japanese Office Action issued Apr. 17, 2012, in Japan Patent Application No. 2007-216893 (with Partial English Translation), English portions only.

* cited by examiner

*Primary Examiner* — Cherie M Stanfield
(74) *Attorney, Agent, or Firm* — Oblon, Spivak, McClelland, Maier & Neustadt, L.L.P.

(57) ABSTRACT

A working unit of a manipulator includes a hollow joint shaft, wires disposed as power transmitting members in the hollow joint shaft, and a distal-end working unit mounted on an end of the hollow joint shaft and movable by the wires. The wires are wound around respective tubular members in the distal-end working unit. The hollow joint shaft has a pair of visual checking holes defined in respective side walls thereof near the distal end thereof for allowing the wires to be visually checked therethrough. The visual checking holes are positioned to expose the tubular members therethrough.

8 Claims, 13 Drawing Sheets

WORKING MECHANISM FOR MEDICAL MANIPULATOR

CROSS-REFERENCE TO RELATED APPLICATION

This application claims priority pursuant to 35 U.S.C. §119 from Japanese Patent Application No. 2007-216893, filed Aug. 23, 2007, which is incorporated by reference in its entirety herein.

BACKGROUND OF THE INVENTION

1. Field of the Invention

The present invention relates to a working mechanism for a medical manipulator, and more particularly to a working mechanism for moving a distal-end working unit of a medical manipulator through filamentary members such as wires or the like.

2. Description of the Related Art

In laparoscopic surgery, a number of small holes are opened in a patient's abdomen or the like, and an endoscope, a forceps (or manipulator) or the like is inserted, and surgery is carried out while the surgeon observes an image from the endoscope on a monitor. In this type of laparoscopic surgery, owing to the fact that opening of the abdominal cavity is unnecessary, the burden on the patient is small, and the number of days required for the post-operative recovery and the number of days spent in the hospital can be significantly reduced. Therefore, laparoscopic surgical operations are expected to find an increased range of applications.

As disclosed in Japanese Laid-Open Patent Publication No. 2004-105451, for example, a manipulator system comprises a manipulator and a controller for controlling the manipulator. The manipulator comprises an operating unit which is manually operable and a working unit replaceably mounted on the operating unit.

The working unit (instrument) comprises a long joint shaft and a distal-end working unit (also referred to as an end effector) mounted on the distal end of the joint shaft. The operating unit has actuators (motors) for actuating the working unit at the distal end through wires. The wires are wound around respective pulleys at a proximal end side. The controller energizes the motors of the operating unit to cause the pulleys to move the wires back and forth.

The working unit is detachably mounted on the operating unit, so that the working unit can easily be processed, e.g., cleaned, after a surgical technique has been performed by the manipulator. In addition, various different working units, including a gripper, scissors, an electrosurgical knife, an ultrasonic knife, a medical drill, etc., are used in a laparoscopic surgical operation process. From the standpoint of being able to exchange these working units, a structure in which the working unit is detachable with respect to the operating unit also is beneficial.

In the working unit, the pulleys on the proximal end side are held in engagement with the rotatable shafts of the motors of the operating unit.

Japanese Laid-Open Patent Publication No. 11-012966 discloses a wire rope including a plurality of discriminant yarns mixed with an outermost layer and each covered with a metallic material which has a color different from the color of surrounding yarns.

The working unit includes pulleys and gears connected together by the wires for simply and reliably transmitting power.

Since the wires are subject to aging or changes due to usage, it is desirable to appropriately judge the degree of aging or usage-induced changes of the wires.

SUMMARY OF THE INVENTION

It is one of the objects of the present invention to provide a working mechanism for a medical manipulator which allows the state of filamentary members for transmitting power to be judged easily and appropriately.

According to one aspect of the present invention, a working mechanism for a medical manipulator includes a filamentary member movable back and forth in ganged relation to an actuator, a hollow shaft, the filamentary member being inserted in the hollow shaft, a distal-end working unit mounted on a distal end of the hollow shaft, the distal-end working unit being operable in response to back-and-forth movement of the filamentary member, and a visual checking area disposed on the hollow shaft near the distal end thereof, for exposing the filamentary member therethrough.

The visual checking area allows a distal end portion of the filamentary member to be visually checked for a change in the state thereof. As the visual checking area serves to allow the operator to visually check the filamentary member in the distal-end working unit, the visual checking area may not necessarily be a physically through hole, but may be covered with a transparent member.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Working mechanisms for a manipulator according to embodiments of the present invention will be described below with reference to FIGS. 1 through 13 of the accompanying drawings.

A medical manipulator 10 (see FIG. 1) has a distal-end working unit 12 for gripping a portion of a living tissue, a curved needle, or the like for performing a certain surgical treatment, and is usually also referred to as gripping forceps or a needle driver (needle holder).

Figure 1:
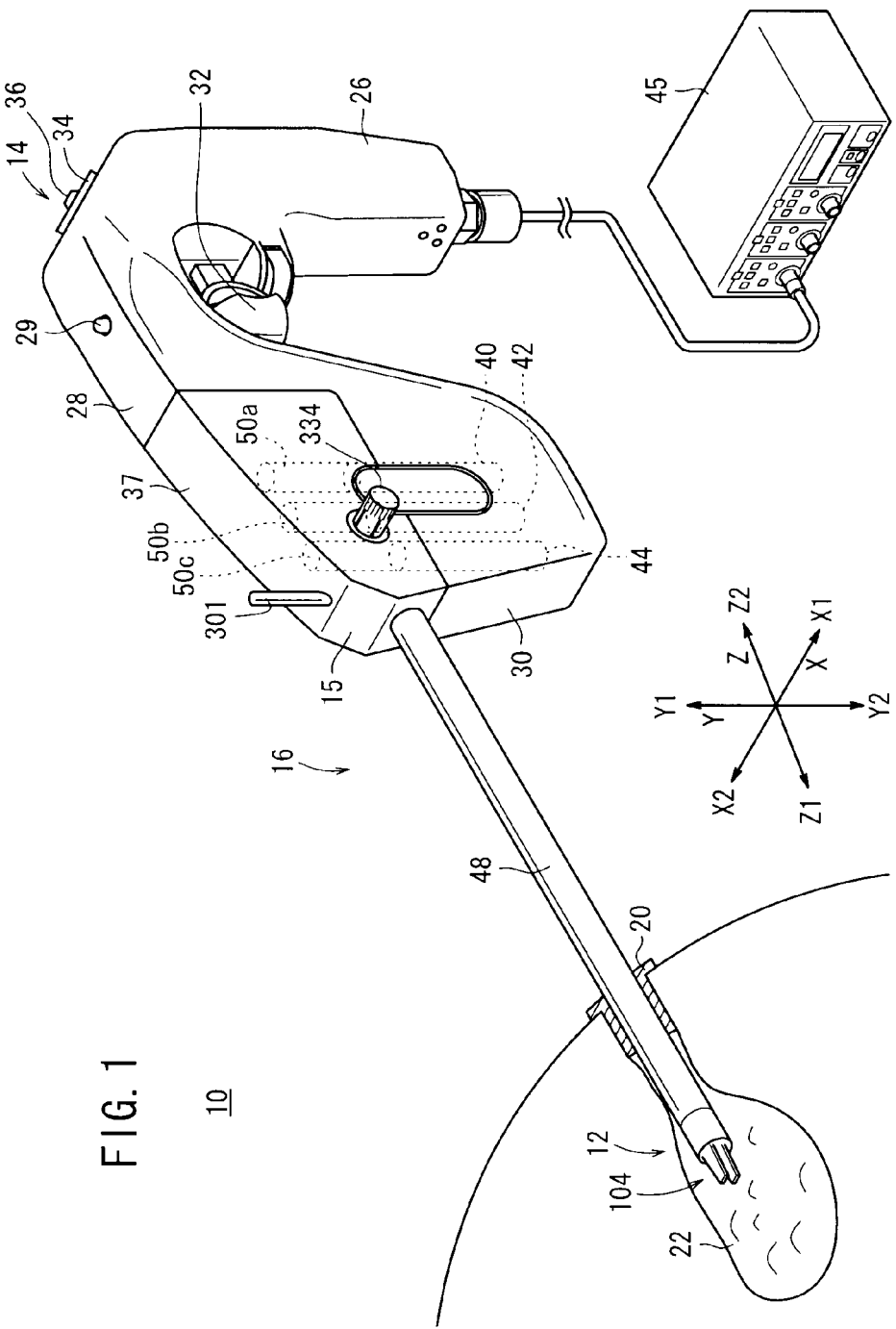
FIG. 1 is a perspective view of a manipulator according to an embodiment of the present invention.
Figure 2:
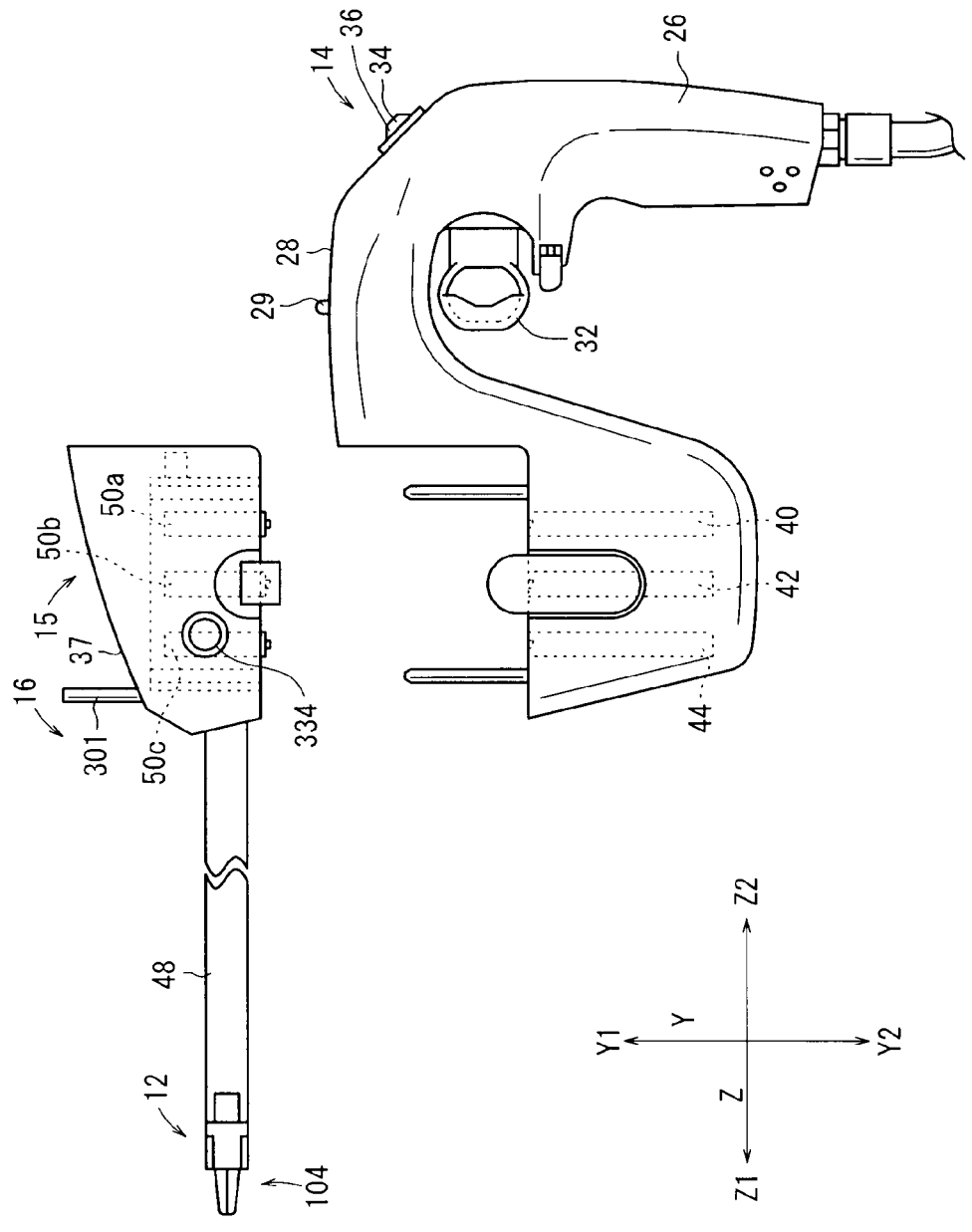
FIG. 2 is a side elevational view of the manipulator with a working unit and an operation command unit being separate from each other.

As shown in FIGS. 1 and 2, the manipulator 10 comprises an operation command unit 14 on a proximal end portion which is held and operated by hand and a working unit (a working mechanism for the medical manipulator) 16 detachably mounted on the operation command unit 14.

It shall be assumed in the following description that, as shown in FIG. 1, the transverse directions are defined as X directions, the vertical directions as Y directions, and the longitudinal directions of a hollow joint shaft 48 as Z directions. Further, among the X directions, the rightward direction is defined as an X1 direction, and the leftward direction as an X2 direction, among the Y directions, the upward direction is defined as a Y1 direction, and the downward direction as a Y2 direction, and among the Z directions, the forward direction is defined as a Z1 direction, and the rearward direction as a Z2 direction. Unless otherwise noted, these directions represent directions of the manipulator 10 when it is of a neutral attitude (attitude shown in FIG. 3). The definition of the above directions is for illustrative purpose only, and the manipulator 10 can be used in any orientations, e.g., it may be used upside down.

The working unit 16 comprises a distal-end working unit 12 for performing working operation, a connector 15 connected to an actuator block 30 of the operation command unit 14, and an elongate hollow joint shaft 48 coupling the distal-end working unit 12 and the connector 15 to each other. When a predetermined action is performed on the actuator block 30, the working unit 16 can be separated from the operation command unit 14, so that the working unit 16 can be cleaned, sterilized, and serviced for maintenance. The distal-end working unit 12 and the joint shaft 48, which are small in diameter, can be inserted into a body cavity 22 through a trocar 20 in the form of a hollow cylinder mounted in an abdominal region or the like of the patient. The distal-end working unit 12 is actuated by the operation command unit 14 to perform various surgical techniques to remove, grip, suture, or ligate (tie-knot) an affected part of the patient's body in the body cavity 22.

The operation command unit 14 includes a grip handle 26 gripped by hand, a bridge 28 extending from an upper portion of the grip handle 26, and the actuator block 30 connected to a distal end of the bridge 28.

The grip handle 26 has a trigger lever 32, a first command lever 34, and a second command lever 36 which can be operated by fingers. The trigger lever 32 is disposed in a position where it can easily be pulled by the index finger of the hand that is gripping the grip handle 26.

The actuator block 30 houses therein a motor (actuator) 40, a motor 42, and a motor 44 associated respectively with mechanisms having three degrees of freedom in the distal-end working unit 12. The motors 40, 42, 44 are juxtaposed along the direction in which the joint shaft 48 extends. The motors 40, 42, 44 are small in size and diameter, and the actuator block 30 which houses the motors 40, 42, 44 therein is of a flat compact shape. The actuator block 30 is disposed below an end of the operation command unit 14 in the Z1 direction. The motors 40, 42, 44 are energized under the control of a controller 45 based on actions made by the operator on the operation command unit 14 and the trigger lever 32.

The connector 15 is covered with a resin cover 37 and houses pulleys 50a, 50b, 50c rotatably supported therein. The pulleys 50a, 50b, 50c have respective lower ends engaging the respective drive shafts of the motors 40, 42, 44, and can be rotated about their own axes by the motors 40, 42, 44. A wire (filamentary member) 52, a wire 54, and a wire 56 are wound respectively around the pulleys 50a, 50b, 50c and extend through a hollow space 48a (see FIG. 3) in the hollow joint shaft 48 to the distal-end working unit 12. The wires 52, 54, 56 may be of the same type and diameter.

The distal-end working unit 12 comprises a composite mechanism 102 and an end effector 104. The wires 52, 54, 56 serve to transmit power to the composite mechanism 102 and the end effector 104 in the distal end of the joint shaft 48.

Figure 3:
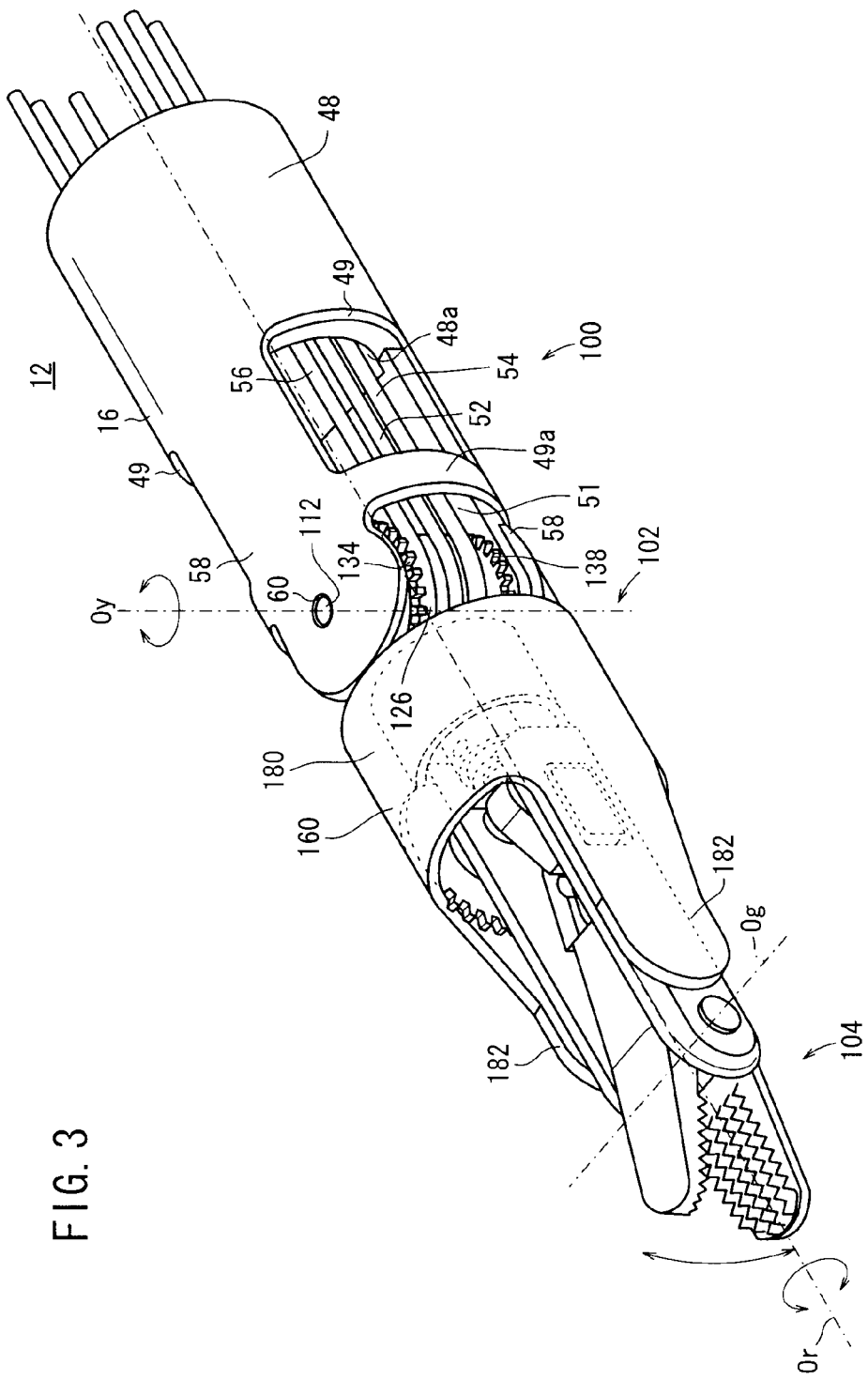
FIG. 3 is a perspective view of a working unit of the manipulator.

As shown in FIG. 3, the distal end of the joint shaft 48 has a pair of visual checking holes (visual checking areas) 49 defined respectively in left and right side walls thereof.

A gap 51 is defined between a cover 160 of the composite mechanism 102 and the joint shaft 48. Gears 134, 138, etc. that are disposed in the distal end of the joint shaft 48 are exposed through the gap 51.

The distal end of the joint shaft 48 has upper and lower tongues 58 that are vertically spaced from each other. The upper and lower tongues 58 are joined to each other by a pair of vertical bridges 49a disposed forwardly of the visual checking holes 49. The gap 51, which extends between the vertical bridges 49a and the cover 160, is small enough to minimize the entry of foreign matter such as living tissues, chemicals, threads, etc. toward the gears 134, 138, etc.

The tongues 58 projecting toward the distal end on the joint shaft 48 are disposed in diametrically facing relation to each other and also to the central axis of the joint shaft 48. The space 48a in the joint shaft 48 communicates with the space defined between the tongues 58. The tongues 58 have respective shaft holes 60 defined therein in alignment with each other. The tongues 58 have respective arcuate edges at their distal ends. The tongues 58 also have respective flat inner surfaces facing each other and lying parallel to each other. The shaft holes 60 are positioned in diametrically opposite relation to each other across the central axis of the joint shaft 48.

As shown in FIG. 3, the distal-end working unit 12 incorporates therein mechanisms of three degrees of freedom. These mechanisms include a mechanism having a first degree of freedom for angularly moving a distal end portion that is positioned ahead of a first rotational axis (pivot axis) Oy extending along the Y directions, in yawing directions about the first rotational axis Oy, a mechanism having a second degree of freedom for angularly moving the distal end portion in rolling directions about a second rotational axis Or extending along the Z directions, and a mechanism having a third degree of freedom for opening and closing the end effector 104 on the distal end about a third rotational axis Og extending along the X directions.

The end effector 104 serves to perform actual actions in a surgical operation, and the first rotational axis Oy and the second rotational axis Or serve to change the attitude of the end effector 104 to facilitate such actual actions. Generally, the mechanism having the third degree of freedom for opening and closing the end effector 104 is also called a gripper axis, the mechanism having the first degree of freedom for angularly moving the distal end portion in the yawing directions is also called a yaw axis, and the mechanism having the second degree of freedom for angularly moving the distal end portion in the rolling directions is also called a roll axis.

Figure 4:
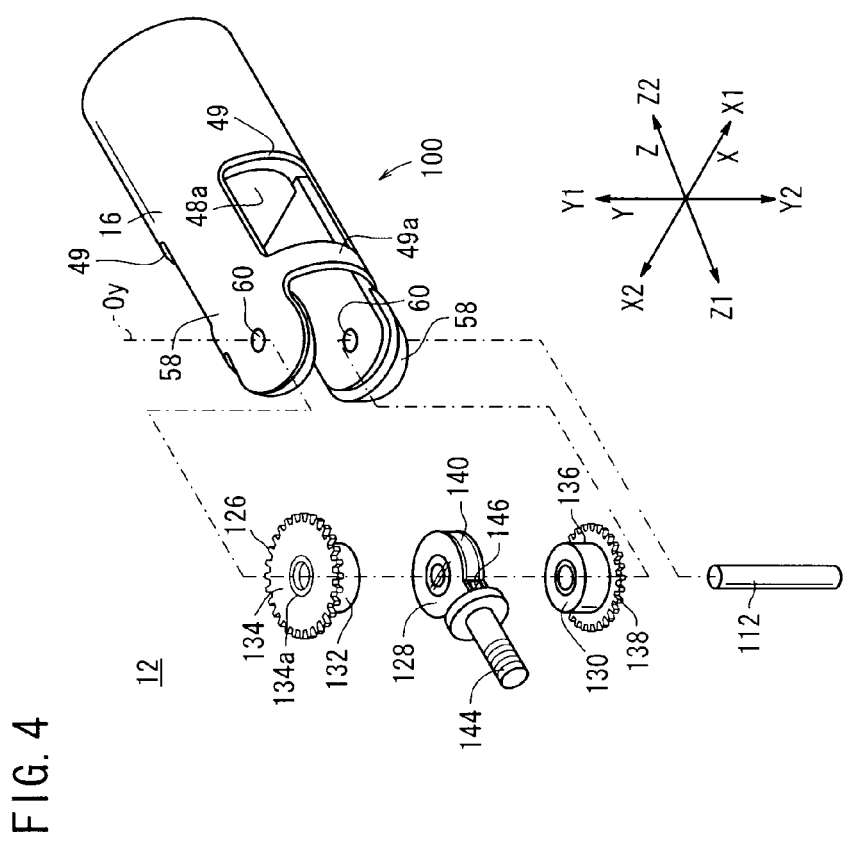
FIG. 4 is an exploded perspective view of a portion of the working unit.

The composite mechanism 102 and the end effector 104 will be described in greater detail with reference to FIGS. 3 and 4.

The composite mechanism 102 is disposed between the tongues 58 for converting the reciprocating movement of the wires 52, 54, 56 into rotary movement, opening and closing the end effector 104, and changing the attitude of the end effector 104. The composite mechanism 102 has a shaft (perpendicular shaft) 112 inserted in the shaft holes 60. The shaft 112 may be secured in place by being press-fitted in the shaft holes 60 or welded to the tongues 58. The shaft 112 is aligned axially with the first rotational axis Oy.

The composite mechanism 102 also has a gear body 126, a main shaft 128, and a gear body 130 which are successively arranged in the order named in the Y2 direction and rotatably supported on the shaft 112.

The gear body 126 comprises a tubular member (rotary member) 132 and a gear 134 disposed concentrically on an upper portion of the tubular member 132. The wire 56 is wound around the tubular member 132 by one or more turns and has a portion fixed to the tubular member 132 so that the wire 56 will not be displaced out of position.

The gear body 130 is essentially identical in shape to the gear body 126, but is in an upside-down orientation with respect to the gear body 126. The gear body 130 comprises a tubular member 136 and a gear 138 disposed concentrically on a lower portion of the tubular member 136. The tubular member 136 is substantially identical in diameter and shape to the tubular member 132. The wire 54 is wound around the tubular member 136 by one or more turns and has a portion fixed to the tubular member 136 so that the wire 54 will not be displaced out of position.

The main shaft 128 has a tubular member 140 through which the shaft 112 extends and a support bar 144 extending from the tubular member 140 in the Z1 direction. The support bar 144 is aligned axially with the second rotational axis Or. The support bar 144 has an externally threaded distal end portion.

A hole 146 is defined in the tubular member 140 for receiving the wire 52 to extend therethrough. The wire 52 is threaded through the hole 146 and wound around the tubular member 140 by one or more turns and has a portion fixed to the tubular member 140 so that the wire 52 will not be displaced out of position.

In response to reciprocating movement of the wire 52, the main shaft 128 rotates in the yawing directions about the first rotational axis Oy to cause the support bar 144 to swing in an XZ plane.

The composite mechanism 102 also includes a mechanism for opening and closing the end effector 104 and moving the end effector 104 in the rolling directions, and the cover 160 covering the mechanism.

The cover 160 serves to protect the parts of the composite mechanism 102 and the end effector 104. The cover 160 comprises a sleeve 180 extending in the Z2 direction and a pair of arms 182 projecting from respective side edges of the sleeve 180 in the Z1 direction. The arms 182 are of an essentially conical shape extending smoothly contiguously from parts of the circumferential wall of the sleeve 180 in the Z1 direction. The cover 160 has a lower portion fixed to the end effector 104 by a cover fastening pin. The cover 160 has a diameter equal to or smaller than the diameter of the joint shaft 48. The cover 160 may be a hollow cylindrical or conical cover covering the end effector 104 essentially in its entirety to such an extent that the cover 160 will not obstruct operation of the end effector 104.

The cover 160 is effective to prevent foreign matter such as living tissues, chemicals, threads, etc. from entering the composite mechanism 102 and the end effector 104.

The visual checking holes 49 of the distal-end working unit 12 will be described below.

Figure 5:
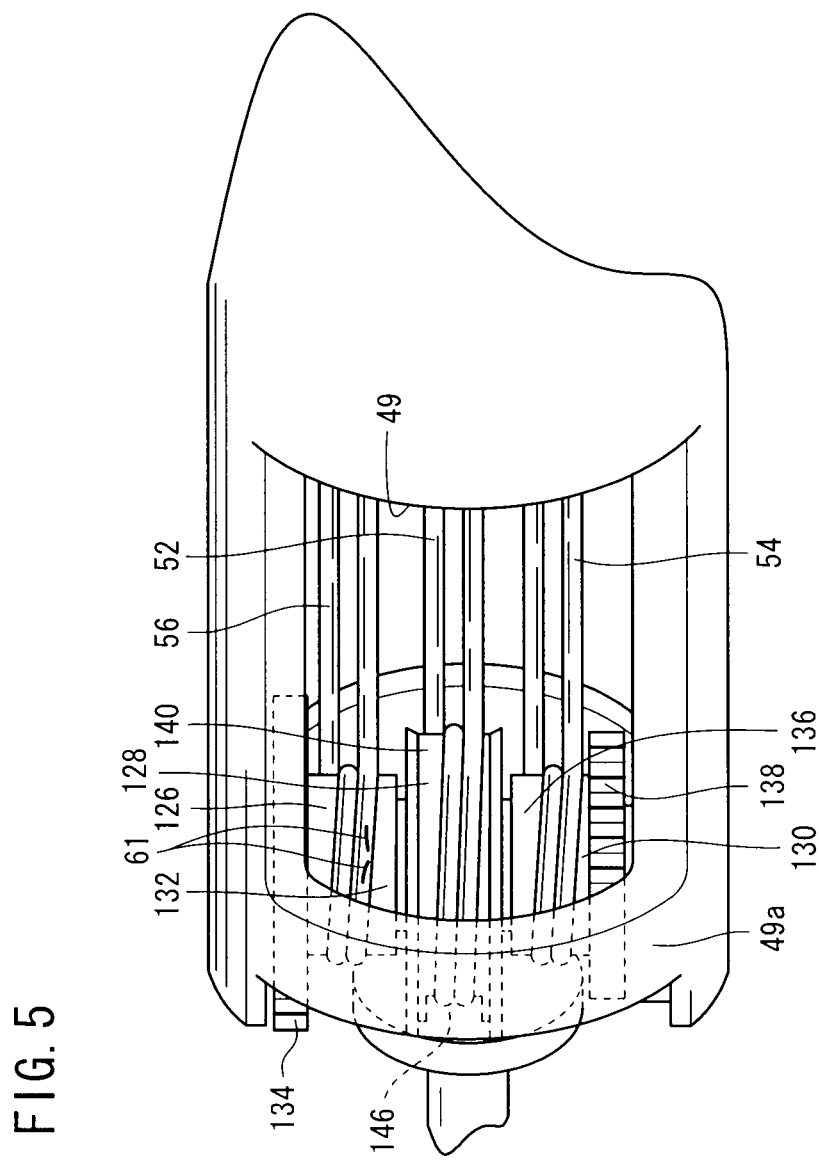
FIG. 5 is a perspective view of a visual checking hole.

As shown in FIG. 5, the visual checking holes 49 are positioned to expose the tubular members 132, 136, 140 for thereby allowing the turns of the wires 52, 54, 56 wound around the tubular members 132, 136, 140 to be visually observed through the visual checking holes 49. The wires 52, 54, 56 can thus easily be visually inspected for breaks 61 of yarns thereof which tend to occur near the tubular members 132, 136, 140. Since the wound turns of the wires 52, 54, 56 are subject to repetitive bending loads from the tubular members 132, 136, 140, the wound turns of the wires 52, 54, 56 are kept under more severe conditions than the other portions of the wires 52, 54, 56. Accordingly, the operator can quickly detect changes in the state of the wires 52, 54, 56 by watching the wires 52, 54, 56 near the tubular members 132, 136, 140.

The visual checking holes 49 are of a rectangular shape having four arcuate corners. The visual checking holes 49 allow the wires 52, 54, 56 to be visually checked for changes in the state thereof. When the operator has found a change in the state of the wires 52, 54, 56 through the visual checking holes 49, the operator can stop using the working unit 16 or service the working unit 16 for maintenance, and can also avoid unnecessarily early stopping of the use of the working unit 16 before its state changes. Since the corners of the visual checking holes 49 are arcuate, they are less likely to catch the suture used in surgical operations and to let the suture go into the visual checking holes 49.

As the visual checking holes 49 serve to allow the operator to visually check the wires 52, 54, 56 in the distal-end working unit 12, the visual checking holes 49 may not necessarily be physically through holes, but may be covered with a transparent member.

Four modifications of the wires 52, 54, 56 will be described below.

Figure 6:
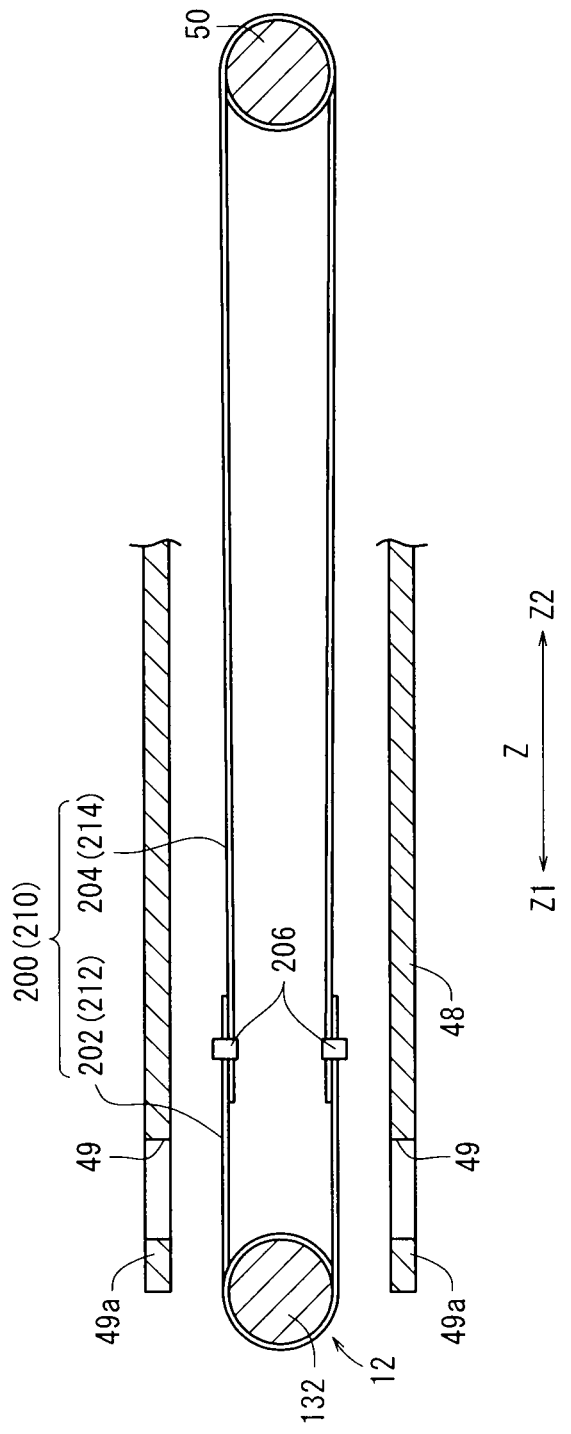
FIG. 6 is a plan view of wires according to first and second modifications.

As shown in FIG. 6, a wire 200 according to a first modification comprises a front wire (first filamentary member) 202 and a rear wire (second filamentary member) 204. The front wire 202 is wound around the tubular member 132 in the distal-end working unit 12, and has at least a portion disposed in the end of the working unit 16 in the Z1 direction such that it can be visually recognized through the visual checking holes 49. The rear wire 204 has ends connected to respective ends of the front wire 202 by sleeves 206, extends in the Z2 direction from the front wire 202, and is wound around the pulley 50. The front wire 202 and the rear wire 204 may be connected to each other by welding or the like.

The front wire 202 is of such a length that the sleeves 206 will not contact the tubular member 132 when the front wire 202 is moved back and forth, and that only the front wire 202, but not the rear wire 204, can be visually recognized through the visual checking holes 49. Also, the front wire 202 is sufficiently short. The front wire 202 is smaller in outside diameter and breaking load than the rear wire 204. For example, the outside diameter of the front wire 202 is about ¾ of the outside diameter of the rear wire 204, and the breaking load of the front wire 202 is about ⅘ of the breaking load of the rear wire 204. The front wire 202 has a sufficient mechanical strength to keep itself trouble-free during normal operation.

Since the front wire 202 is wound around the tubular member 132 and the rear wire 204 is wound around the pulley 50, they are subject to essentially the same bending stresses. However, as the breaking load of the front wire 202 is smaller than the breaking load of the rear wire 204, the front wire 202 is more likely to start changing in its state than the rear wire 204. Consequently, only the front wire 202 needs to be observed. A change in the state of the front wire 202 can easily be confirmed because almost the entire length of the front wire 202 can visually be recognized through the visual checking holes 49. The distal-end working unit 12 may be made compact because the front wire 202 is smaller in outside diameter than the rear wire 204.

As shown in FIG. 6, a wire 210 according to a second modification comprises a front wire (first filamentary member) 212 and a rear wire (second filamentary member) 214. Since the wire 210 is apparently identical to the wire 200 according to the first modification, the wire 210 is illustrated as the same as the wire 200. The front wire 212 and the rear wire 214 have respective lengths which are the same as the lengths of the front wire 202 and the rear wire 204 according to the first modification.

Figure 7:
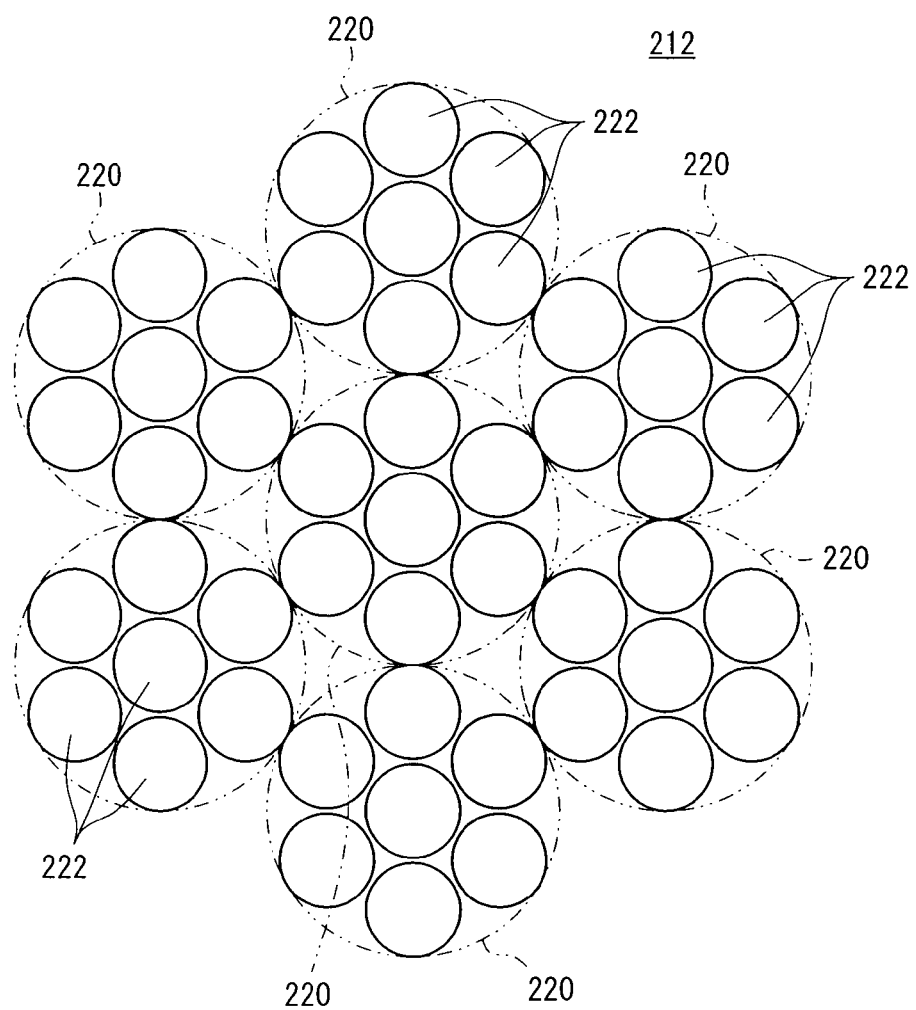
FIG. 7 is an enlarged transverse cross-sectional view of a front wire.
Figure 8:
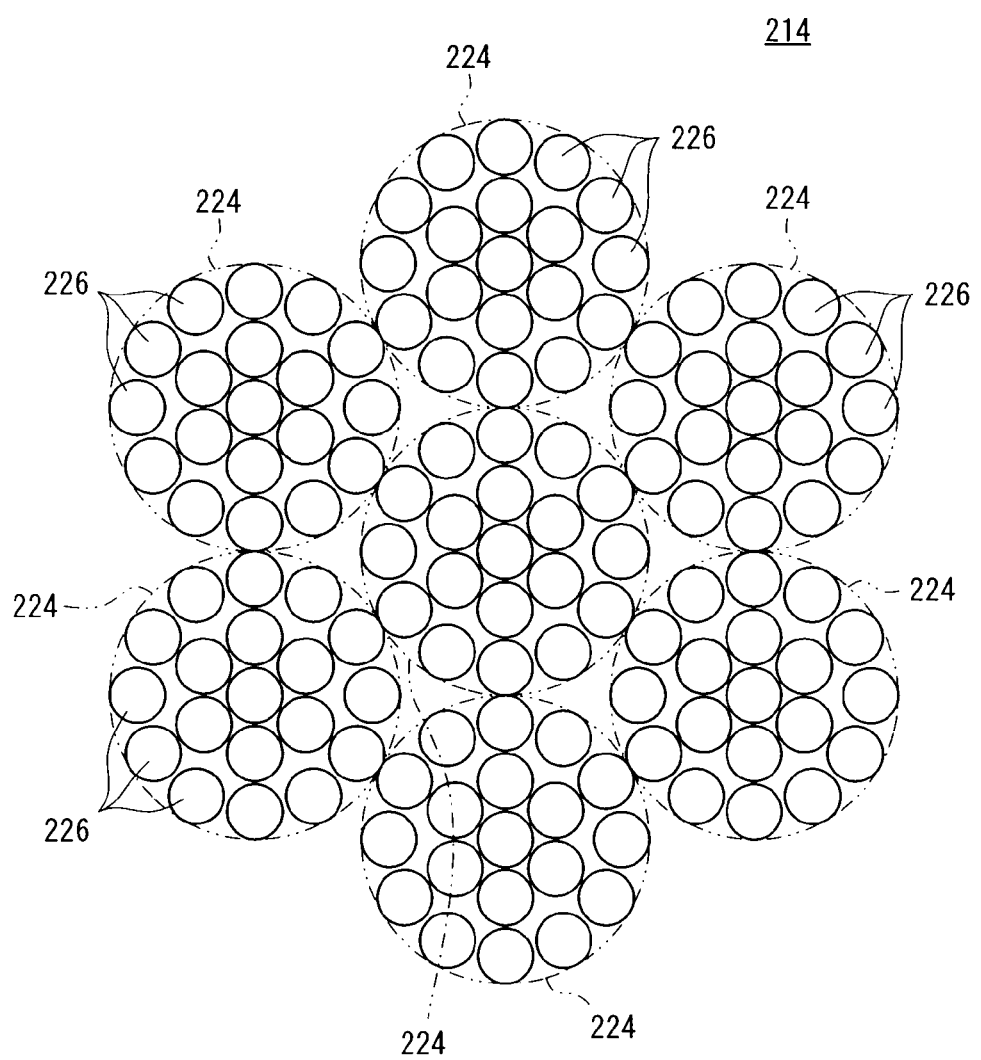
FIG. 8 is an enlarged transverse cross-sectional view of a rear wire.

As shown in FIGS. 7 and 8, the front wire 212 is of substantially the same outside diameter than the rear wire 214. However, the front wire 212 is different in yarn configuration than the rear wire 214, and is harder in bending directions and less flexible than the rear wire 214.

Figure 12:
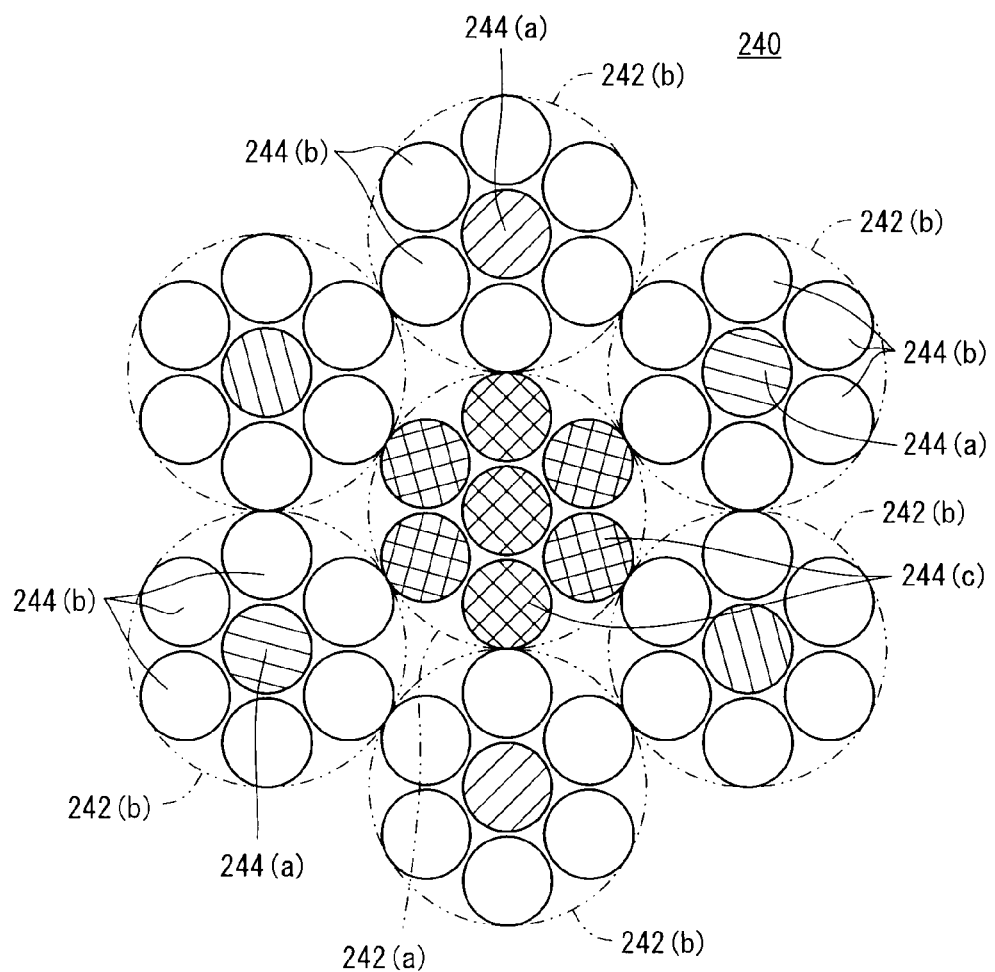
FIG. 12 is an enlarged transverse cross-sectional view of a wire according to a fourth modification.
Figure 13:
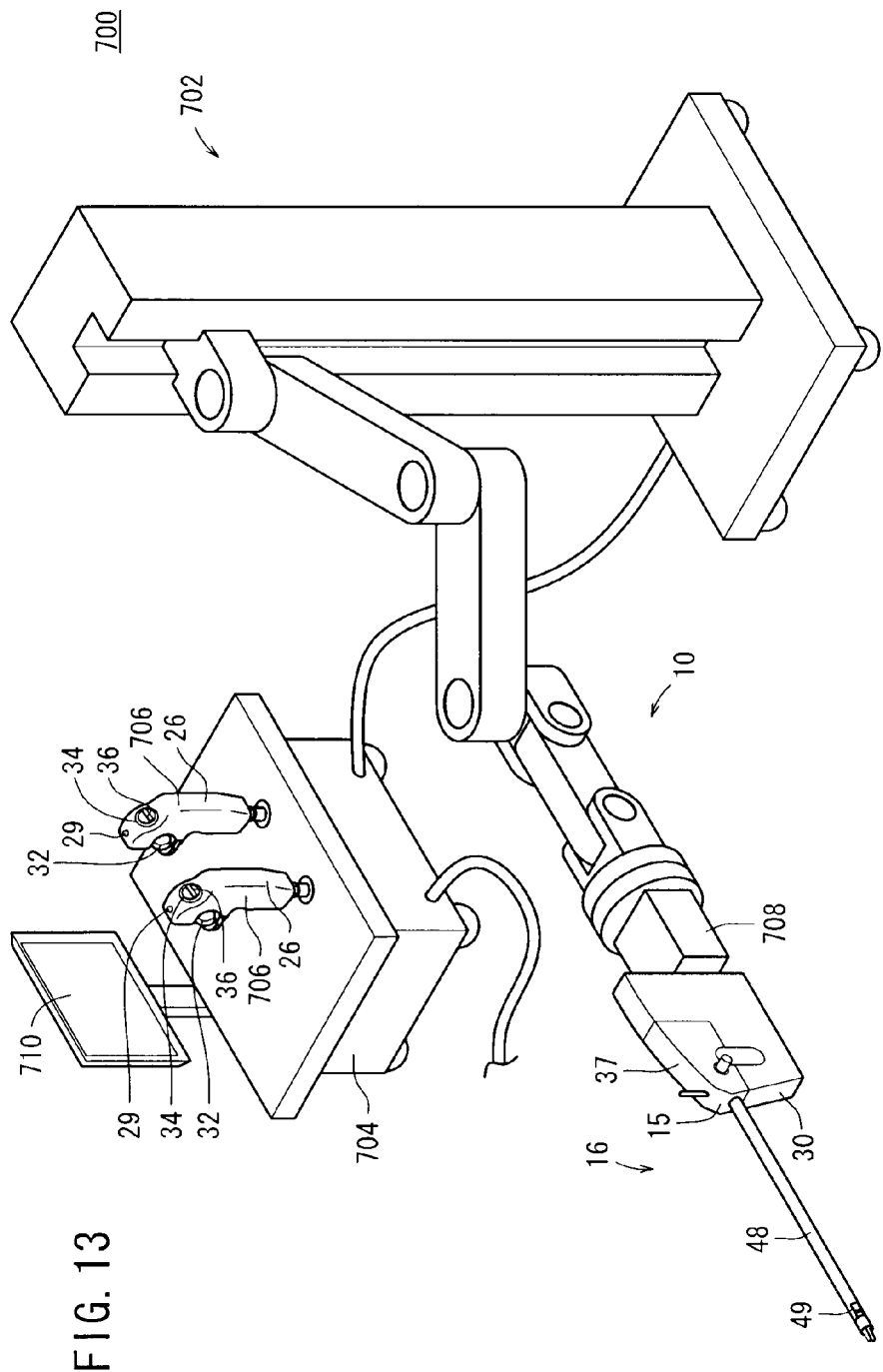
FIG. 13 is a schematic perspective view of a surgical robot system with a working unit connected to the distal end of a robot arm.

As shown in FIG. 7, the front wire 212 comprises seven strands 220 that are twisted together. Each of the strands 220 comprises seven yarns 222 that are twisted together. In FIGS. 7, 8, and 12, imaginary lines indicative of the strands 220, 224 and 242 are shown for illustrative purposes only.

As shown in FIG. 8, the rear wire 214 comprises seven strands 224 that are twisted together. Each of the strands 224 comprises 19 yarns 226 that are twisted together.

In other words, the front wire 212 comprises a total of 49 yarns 222, and the rear wire 214 comprises a total of 133 yarns 226. The yarns 226 are considerably smaller in diameter than the yarns 222. When a bending load is applied to the front wire 212 and the rear wire 214, a force per yarn applied to the yarns 222 of the front wire 212 is larger than that applied to the yarns 226 of the rear wire 214. The front wire 212 is less flexible than the rear wire 214.

The front wire 212 is wound around the tubular member 132, and the rear wire 214 is wound around the pulley 50. The front wire 212 and the rear wire 214 are subject to essentially the same bending stresses. However, as the front wire 212 is less flexible than the rear wire 214, the front wire 212 is more likely to start changing in its state than the rear wire 214. Since the front wire 212 initially starts changing in its state, only the front wire 212 needs to be observed.

It is not necessary for the yarns 222 of the front wire 212 to be identical in diameter to each other or for the yarns 226 of the rear wire 214 to be identical in diameter to each other. If the yarns 222 are of different diameters and the yarns 226 are of different diameters, then the yarns 222 may be smaller in average diameter than the rear yarns 226.

Figure 9:
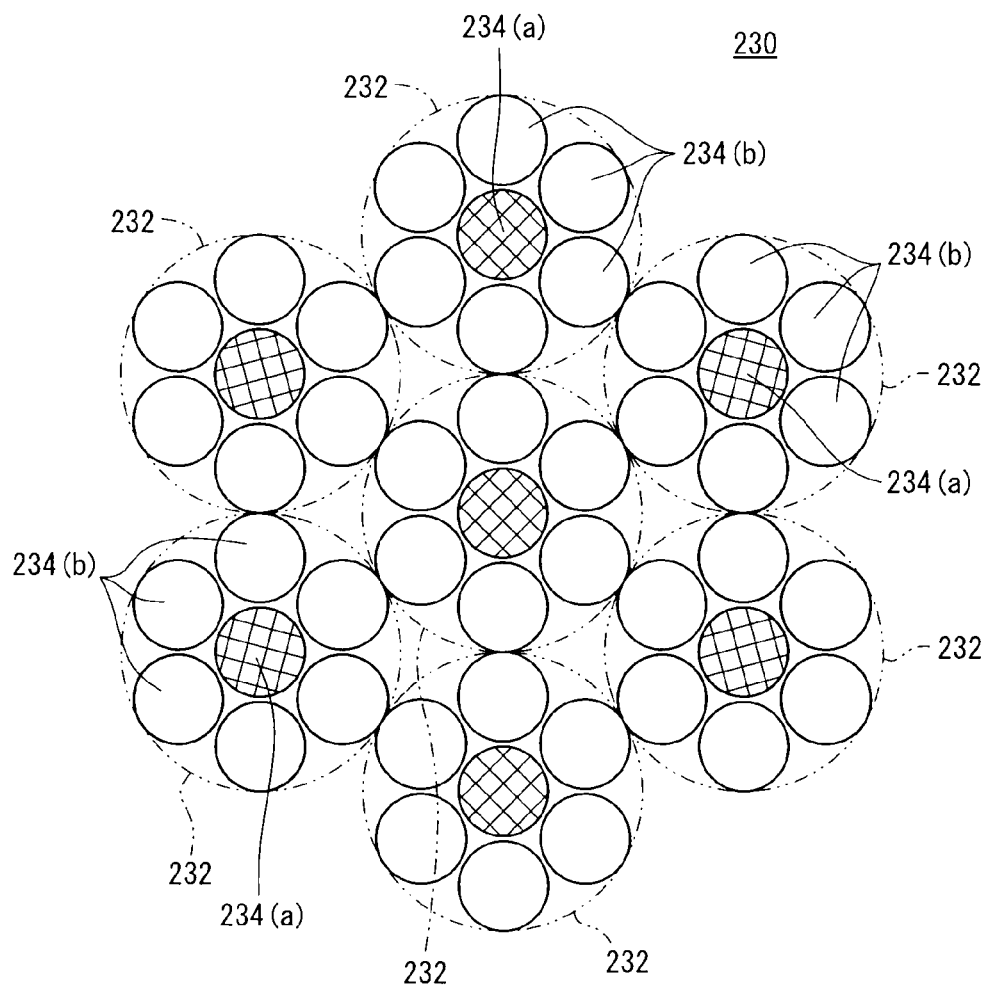
FIG. 9 is an enlarged transverse cross-sectional view of a wire according to a third modification.

As shown in FIG. 9, a wire 230 according to a third embodiment comprises seven strands 232 that are twisted together. Each of the strands 232 comprises seven yarns 234 that are twisted together. Of the seven yarns 234, the central yarn 234a is not twisted. The other six yarns 234b are twisted around the central yarn 234a. The surrounding six yarns 234b appear on the surface of each of the strands 232, and the central yarn 234a does not appear on the surface of each of the strands 232.

Figure 10:
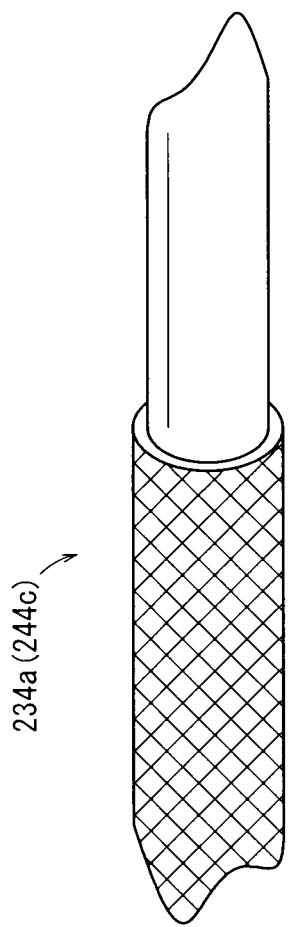
FIG. 10 is an enlarged fragmentary perspective view of a yarn.

Each of the surrounding yarns 234b has a surface exhibiting a metallic ground color. As shown in FIG. 10, each of the central yarns 234a has a colored covering such as a resin covering whose surface is red in color. In FIG. 10, the color red is shown cross-hatched. The colored covering may be made of any materials that are harmless to the living body, and should preferably be of a prominent color.

Figure 11:
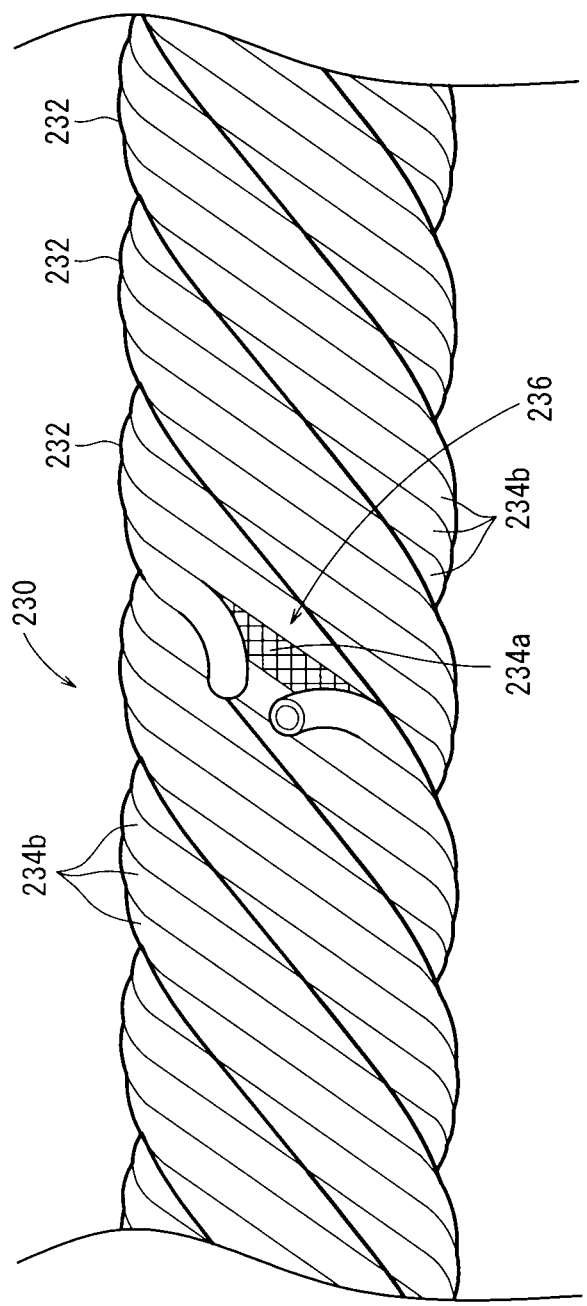
FIG. 11 is an enlarged fragmentary perspective view of the wire according to the third modification with a yarn being broken.

When the wire 230 changes in its state due to usage and one of the yarns 234b is broken, as shown in FIG. 11, the red color of the central yarn 234a behind the broken yarn 234b is visually recognized through a broken region 236, providing a sharp contrast with the metallic color of the other yarns 234b. Therefore, the broken region 236 can easily be recognized. The broken region 236 tends to occur in the distal end portion of the working unit 16, and can be confirmed through the visual checking holes 49.

Not all the yarns 234a need to have a red colored covering, but parts of the yarns 234a may have a red colored covering. For example, the yarn 234a of the central strand 232 may not have a red colored covering.

As shown in FIG. 12, a wire 240 according to a fourth modification comprises seven strands 242 that are twisted together. Each of the strands 242 comprises seven yarns 244 that are twisted together. Of the seven strands 242, the central strand 242a is not twisted, and the other six strands 242b are twisted around the central strand 242a. Of the seven yarns 244, the central yarn 244a is not twisted, and the other six yarns 244b are twisted around the central yarn 244a. The surrounding six strands 242b appear on the surface of the wire 240, and the central strand 242a does not appear on the surface of the wire 240. The surrounding six yarns 244b appear on the surface of the strand 242, and the central yarn 244a does not appear on the surface of the strand 242.

Each of the surrounding yarns 244b of each of the surrounding strands 242b has a surface exhibiting a metallic ground color. The central yarn 244a of each of the surrounding strands 242b has a colored covering whose surface is yellow in color (first color). The colored covering is of the same material as the colored covering shown in FIG. 10.

Each of the yarns 244c of the central strand 242a has a colored covering whose surface is red in color (second color) (see FIG. 10). Alternatively, instead of each of the yarns 244c, the central strand 242a itself may have a red colored covering.

When the wire 240 changes in its state due to usage and one of the yarns 244b is broken, the yellow color of the central yarn 244a behind the broken yarn 244b is visually recognized, providing a sharp contrast with the metallic color of the other yarns 244b. Therefore, the broken region can easily be recognized. Even when one of the yarns 244b of the strands 242b on the surface of the wire 240 is broken, the mechanical strength of the wire 240 remains strong enough to let the wire 240 be used continuously. If the number of broken regions where the yellow color is visually recognizable increases and exceeds a certain criterion, then the operator takes a certain action, e.g., stops using the working unit 16.

However, when at least one of the strands 242 is broken, the operator stops using the working unit 16. When one of the strands 242 is broken, the red color of the central strand 242a is visually recognized. Therefore, the operator can easily recognize when to stop using the working unit 16.

Accordingly, the wire 240 indicates stepwise, by different colors, that the time to stop using the working unit 16 is approaching and also that use of the working unit 16 should be stopped. Of course, before the red color of the central strand 242a is visually recognized, the operator may stop using the working unit 16 when the number of broken regions where the yellow color is visually recognizable increases and exceeds a certain criterion.

The yarns and strands may be colored in colors other than red and yellow insofar as those colors are essentially different from the ground color of the yarns. For example, the yarns and strands may be colored in colors which are different by 10 hues, 3 values, and 3 chromas according to the Munsell color system.

In FIGS. 9 and 12, the color red is shown cross-hatched and the color yellow hatched in the cross section of the yarns. Actually, the surfaces of the yarns are red or yellow in color.

As described above, the distal-end working unit 12 of the medical manipulator 10 according to the present invention has the visual checking holes 49 defined in the joint shaft 48 near its distal end for allowing the wires 52 through 56, 200, 210, 230, 240 to be visually checked through the visual checking holes 49. Thus, a change in the state of those wires can easily be inspected.

The working unit 16 has been described as connected to the operation command unit 14 that is manually operable. However, the working unit 16 may be applied to a surgical robot system 700 shown in FIG. 13, for example.

The surgical robot system 700 has an articulated robot arm 702 and a console 704 with the working unit 16 connected to the distal end of the robot arm 702. The distal end of the robot arm 702 incorporates therein a mechanism which is the same as the actuator block 30 for connecting and actuating the working unit 16. The manipulator 10 comprises the robot arm 702 and the working unit 16. The robot arm 702 may be a means for moving the working unit 16, and is not limited to an installed type, but may be of an autonomous movable type. The console 704 may be of a table type, a control panel type, or the like.

The robot arm 702 should preferably have independent six or more joints (rotary shafts, slide shafts, etc.) for setting the position and orientation of the working unit 16 as desired. The actuator block 30 on the distal end of the robot arm 702 is integrally combined with a distal end 708 of the robot arm 702.

The robot arm 702 operates under the console 704, and may be automatically actuatable according to a program, or by joysticks 706 mounted on the console 704, or by a combination of the program and the joysticks 706. The console 704 includes the function of the controller 45.

The console 704 includes the two joysticks 706 as an operation command unit exclusive of the actuator block 30 of the above operation command unit 14, and a monitor 710. Though not shown, the two joysticks 706 are capable of individually operating two robot arms 702. The two joysticks 706 are disposed in respective positions where they can easily be operated by the both hands of the operator. The monitor 710 displays information such as an image produced by an endoscope.

The joysticks 706 can be moved vertically and horizontally, twisted, and tilted, and the robot arm 702 can be moved depending on these movements of the joysticks 706. The joysticks 706 can be operated in the same manner as with the operation command units 14, by the trigger levers 32, the first command lever 34, and the second command lever 36 on the grip handles 26. The joysticks 706 may be master arms. The robot arm 702 and the console 704 may communicate with each other via a communication means comprising a wired link, a wireless link, a network, or a combination thereof. The visual checking holes 49 are defined in the laterally spaced side walls of the distal-end working unit 12.

Although certain preferred embodiments of the present invention have been shown and described in detail, it should be understood that various changes and modifications may be made therein without departing from the scope of the appended claims.

What is claimed is:

1. A working mechanism for a medical manipulator, comprising:
   a filamentary member movable back and forth in ganged relation to an actuator;
   a hollow shaft, the filamentary member being inserted in the hollow shaft;
   a distal-end working unit mounted on a distal end of the hollow shaft, the distal-end working unit being operable in response to back-and-forth movement of the filamentary member, the filamentary member being wound around a rotary member in the distal-end working unit; and
   a visual checking area disposed on the hollow shaft so that at least a rear portion of the rotary member is exposed therethrough, the rear portion being positioned opposite to the distal-end working unit, for exposing the filamentary member therethrough.

2. The working mechanism according to claim 1, wherein the filamentary member comprises:
   a first filamentary member wound around the rotary member in the distal-end working unit and having at least a portion visually recognizable through the visual checking area; and
   a second filamentary member having ends connected to ends of the first filamentary member and extending toward the actuator, and
   wherein the first filamentary member is smaller in breaking load than the second filamentary member.

3. The working mechanism according to claim 1, wherein the filamentary member comprises:
   a first filamentary member wound around the rotary member in the distal-end working unit and having at least a portion visually recognizable through the visual checking area; and
   a second filamentary member having ends connected to ends of the first filamentary member and extending toward the actuator, and
   wherein the first filamentary member and the second filamentary member each includes a plurality of yarns, and the first filamentary member is greater in average diameter of yarns than the second filamentary member.

4. The working mechanism according to claim 1, wherein the filamentary member comprises a plurality of yarns twisted together, the yarns including yarns appearing on a surface of the filamentary member and yarns not appearing on the surface of the filamentary member, and
   wherein at least one of the yarns not appearing on the surface of the filamentary member has a color different from colors of the yarns appearing on the surface of the filamentary member so that when at least one of the yarns appearing on the surface is broken, the at least one of the yarns not appearing on the surface is exposed to show the different color.

5. The working mechanism according to claim 4, wherein the at least one of the yarns not appearing on the surface of the filamentary member has a resin covering of the different color.

6. The working mechanism according to claim 1, wherein the filamentary member comprises a plurality of strands twisted together, the strands including strands appearing on a surface of the filamentary member and strands not appearing on the surface of the filamentary member, and wherein at least one of the strands not appearing on the surface of the filamentary member has a color different from colors of the strands appearing on the surface of the filamentary member, so that when at least one of the strands appearing on the surface is broken, the at least one of the strands not appearing on the surface is exposed to show the different color.

7. The working mechanism according to claim 6, wherein the at least one of the strands not appearing on the surface of the filamentary member has a resin covering of the different color on the at least one of the strands not appearing on the surface of the filamentary member itself or on yarns thereof.

8. The working mechanism according to claim 1, wherein the filamentary member comprises a plurality of strands twisted together, wherein each of the strands comprises a plurality of yarns twisted together, wherein the yarns include yarns appearing on a surface of the filamentary member and yarns not appearing on the surface of the filamentary member, and at least one of the yarns not appearing on the surface of the filamentary member has a first color different from colors of the yarns appearing on the surface of the filamentary member, and wherein the strands include at least one strand not appearing on the surface of the filamentary member, and the at least one strand has a second color different from the colors of the yarns appearing on the surface of the filamentary member and the first color of the at least one of the yarns, so that when at least one of the yarns appearing on the surface is broken, the at least one of the yarns not appearing on the surface or the at least one strand not appearing on the surface is exposed to show the first color or the second color.

\* \* \* \* \*